(12) United States Patent
Bonn et al.

(10) Patent No.: US 8,992,413 B2
(45) Date of Patent: Mar. 31, 2015

(54) MODIFIED WET TIP ANTENNA DESIGN

(75) Inventors: Kenlyn S. Bonn, Arvada, CO (US);
Darion R. Peterson, Boulder, CO (US);
Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 891 days.

(21) Appl. No.: 13/118,929

(22) Filed: May 31, 2011

(65) Prior Publication Data

US 2012/0310228 A1    Dec. 6, 2012

(51) Int. Cl.
*A61B 18/18* (2006.01)
*A61B 18/00* (2006.01)

(52) U.S. Cl.
CPC ... *A61B 18/1815* (2013.01); *A61B 2018/00023* (2013.01); *A61B 2018/1838* (2013.01); *A61B 2018/1869* (2013.01); *A61B 2018/1892* (2013.01); *A61B 2018/00577* (2013.01)
USPC .......................................... 600/33; 607/101

(58) Field of Classification Search
CPC ............. A61B 2018/0005; A61B 2018/00011; A61B 2018/00017; A61B 2018/00023; A61B 2018/04; A61B 2018/18; A61B 2018/1815; A61B 2018/1838; A61B 2018/1846; A61B 2018/1853; A61B 18/18; A61B 18/1815
USPC ............................. 606/33; 607/101–105, 156
See application file for complete search history.

(56) References Cited

U.S. PATENT DOCUMENTS

| D223,367 S | 4/1972 | Kountz |
| D263,020 S | 2/1982 | Rau, III |
| D266,842 S | 11/1982 | Villers et al. |
| D278,306 S | 4/1985 | McIntosh |

(Continued)

FOREIGN PATENT DOCUMENTS

| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Joseph Stoklosa
*Assistant Examiner* — Eunhwa Kim

(57) ABSTRACT

A microwave antenna including a feedline, a radiating section, an inflow hypotube, a puck, a transition collar and a sleeve. The feedline includes a coaxial cable including an inner and outer conductor, and a dielectric disposed therebetween. The radiating section includes a dipole antenna coupled to the feedline and a trocar coupled to the distal end of the dipole antenna. The inflow hypotube is disposed around the outer conductor and configured to supply fluid to the radiating portion. The puck includes at least two ribs with inflow slots defined between two adjacent ribs. The transition collar is coupled to the distal end of the inflow hypotube and the first end of the puck. The transition collar includes at least two outflow slots configured to receive fluid from a distal end of the inflow hypotube and to transition the fluid from the outflow slots to a distal end of the radiating section. The sleeve overlays the two outflow slots of the transition collar, the puck and at least the distal portion of the radiating section. The sleeve forms a fluid-tight seal with the transition collar proximal the outflow slots and defines a first gap for transitioning the fluid to exit the outflow slots of the transition collar to the distal end of the radiating section.

18 Claims, 10 Drawing Sheets

(56) References Cited

U.S. PATENT DOCUMENTS

| | | | |
|---|---|---|---|
| 4,658,836 A | 4/1987 | Turner | |
| D295,893 S | 5/1988 | Sharkany et al. | |
| D295,894 S | 5/1988 | Sharkany et al. | |
| 5,275,597 A | 1/1994 | Higgins et al. | |
| 5,370,677 A | 12/1994 | Rudie et al. | |
| D354,218 S | 1/1995 | Van de Peer | |
| 5,609,151 A | 3/1997 | Mulier et al. | |
| 5,951,546 A | 9/1999 | Lorentzen | |
| D424,693 S | 5/2000 | Pruter | |
| D424,694 S | 5/2000 | Tetzlaff et al. | |
| D425,201 S | 5/2000 | Tetzlaff et al. | |
| 6,056,744 A | 5/2000 | Edwards | |
| 6,117,101 A | 9/2000 | Diederich et al. | |
| 6,134,476 A | 10/2000 | Arndt et al. | |
| 6,175,768 B1 | 1/2001 | Arndt et al. | |
| 6,230,060 B1 | 5/2001 | Mawhinney | |
| 6,273,886 B1 | 8/2001 | Edwards et al. | |
| D449,886 S | 10/2001 | Tetzlaff et al. | |
| 6,308,091 B1 | 10/2001 | Avitall | |
| 6,330,479 B1 | 12/2001 | Stauffer | |
| 6,358,245 B1 | 3/2002 | Edwards et al. | |
| D457,958 S | 5/2002 | Dycus et al. | |
| D457,959 S | 5/2002 | Tetzlaff et al. | |
| 6,413,255 B1 | 7/2002 | Stern | |
| 6,514,249 B1 | 2/2003 | Maguire et al. | |
| 6,547,788 B1 | 4/2003 | Maguire et al. | |
| 6,599,288 B2 | 7/2003 | Maguire et al. | |
| 6,610,054 B1 | 8/2003 | Edwards et al. | |
| 6,652,515 B1 | 11/2003 | Maguire et al. | |
| 6,673,070 B2 | 1/2004 | Edwards et al. | |
| D487,039 S | 2/2004 | Webster et al. | |
| 6,786,905 B2 | 9/2004 | Swanson et al. | |
| D496,997 S | 10/2004 | Dycus et al. | |
| D499,181 S | 11/2004 | Dycus et al. | |
| 6,852,091 B2 | 2/2005 | Edwards et al. | |
| 6,866,624 B2 | 3/2005 | Chornenky et al. | |
| 6,905,510 B2 | 6/2005 | Saab | |
| 6,974,463 B2 | 12/2005 | Magers et al. | |
| 6,997,925 B2 | 2/2006 | Maguire et al. | |
| D525,361 S | 7/2006 | Hushka | |
| 7,089,063 B2 | 8/2006 | Lesh et al. | |
| D531,311 S | 10/2006 | Guerra et al. | |
| 7,122,031 B2 | 10/2006 | Edwards et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,294,127 B2 | 11/2007 | Leung et al. | |
| 7,309,336 B2 | 12/2007 | Ashley et al. | |
| 7,311,703 B2 * | 12/2007 | Turovskiy et al. | 606/33 |
| 7,326,201 B2 | 2/2008 | Fjield et al. | |
| D564,662 S | 3/2008 | Moses et al. | |
| 7,410,486 B2 | 8/2008 | Fuimaono et al. | |
| D576,932 S | 9/2008 | Strehler | |
| 7,467,075 B2 | 12/2008 | Humphries et al. | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| 7,875,024 B2 | 1/2011 | Turovskiy et al. | |
| D634,010 S | 3/2011 | DeCarlo | |
| 2003/0096936 A1* | 5/2003 | Wu et al. | 528/76 |
| 2005/0033278 A1 | 2/2005 | McClurken et al. | |
| 2005/0149010 A1 | 7/2005 | Turovskiy et al. | |
| 2006/0015162 A1 | 1/2006 | Edward et al. | |
| 2009/0187180 A1* | 7/2009 | Brannan | 606/33 |
| 2009/0295674 A1 | 12/2009 | Bonn | |
| 2009/0306652 A1 | 12/2009 | Buysse et al. | |
| 2010/0101825 A1 | 4/2010 | Bonn | |
| 2010/0305559 A1 | 12/2010 | Brannan et al. | |
| 2010/0321257 A1 | 12/2010 | Brannan | |
| 2011/0034917 A1 | 2/2011 | Brannan | |
| 2011/0056069 A1 | 3/2011 | Bonn | |
| 2011/0066144 A1* | 3/2011 | Bonn et al. | 606/33 |
| 2011/0098695 A1 | 4/2011 | Brannan | |
| 2011/0098696 A1 | 4/2011 | Brannan | |
| 2011/0098697 A1 | 4/2011 | Brannan | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 1 186 274 A2 | 3/2002 |
| EP | 0 648 515 | 4/2003 |
| EP | 2 255 742 A1 | 12/2010 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |

(56) References Cited

FOREIGN PATENT DOCUMENTS

| JP | 2000350732 | 12/2000 |
|---|---|---|
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO 96/18349 | 6/1996 |
| WO | WO 00/48672 | 8/2000 |
| WO | WO 00/53113 | 9/2000 |
| WO | WO 02/45790 A2 | 6/2002 |
| WO | WO 03/024309 A2 | 3/2003 |
| WO | WO 2005/011049 A2 | 2/2005 |
| WO | WO 2008/002517 A1 | 1/2008 |
| WO | WO2010/035831 | 4/2010 |

OTHER PUBLICATIONS

U.S. Appl. No. 08/483,742, filed Jun. 7, 1995, Roger A. Stern.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/098,199, filed Apr. 29, 2011, Roop L. Mahajan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.

(56) References Cited

OTHER PUBLICATIONS

Crawford et al., "Use of the LigaSure™ Vessel Sealing System in Urologic Cancer Surger" Grand Rounds in Urology 1999, vol. 1, Issue 4, pp. 10-17.

Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline, "Light Key Projection Keyboard" 2004 Advanced Input Systems, located at: <http://www.advanced-input.com/lightkey> last visited on Feb. 10, 2005.

Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al. (1995) "Saline-enhanced RF Ablation: Demonstration of Efficacy and Optimization of Parameters", Radiology, 197(P): 140 (Abstr).

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Humphries Jr. et al., "Finite•Element Codes to Model Electrical Heating and Non•Llnear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College of Surgeons (ACS) Clinic La Congress Poster (2000).

Johnson et al., "New Low-Profile Applicators for Local Heating of Tissues", IEEE Transactions on Biomedical Engineering, vol. BME-31, No. 1, Jan. 1984, pp. 28-37.

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing".Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, p. 140 (Abstr).

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

(56) References Cited

OTHER PUBLICATIONS

Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.

(56) References Cited

OTHER PUBLICATIONS

European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
European Search Report Application No. EP 12 00 4169 dated Aug. 31, 2012.

* cited by examiner

MODIFIED WET TIP ANTENNA DESIGN

BACKGROUND

1. Technical Field

The present disclosure relates generally to microwave applicators used in tissue ablation procedures. More particularly, the present disclosure is directed to a modified version of a choked wet-tip ablation antenna.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antennas that penetrate tissue to reach tumors. There are several types of microwave antennas, such as monopole and dipole. In monopole and dipole antennas, microwave energy radiates perpendicularly from the axis of the conductor. A monopole antenna includes a single, elongated microwave conductor. Dipole antennas typically have a coaxial construction including an inner conductor and an outer conductor separated by a dielectric portion. More specifically, dipole microwave antennas include a long, thin inner conductor that extends along a longitudinal axis of the antenna and is surrounded by an outer conductor. In certain variations, a portion or portions of the outer conductor may be selectively removed to provide for more effective outward radiation of energy. This type of microwave antenna construction is typically referred to as a "leaky waveguide" or "leaky coaxial" antenna.

A typical tissue-penetrating (i.e., percutaneously inserted) microwave energy delivery device includes a transmission portion formed by a long, thin inner conductor that extends along the axis of the device. The inner conductor is surrounded by a dielectric material and the outer conductor is radially-disposed relative to the dielectric material and forms a coaxial waveguide for transmitting a microwave signal. The distal end of the transmission portion of the outer conductor connects to a microwave antenna configured to receive the microwave signal from the transmission portion and to radiate the microwave energy signal to tissue.

Structural strength is provided to the microwave energy delivery device by surrounding at least part of the transmission portion and/or the microwave antenna with a high-strength jacket. The distal end of the high-strength jacket may connect to, or form, a sharpened tip for piercing tissue.

Invasive procedures have been developed in which the microwave antenna delivery device is inserted directly into a point of treatment via percutaneous insertion. Such invasive procedures potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growths of cells. However, at slightly elevated temperatures above the approximate range of 43° C. to 45° C., thermal damage to most types of normal cells is routinely observed; accordingly, great care must be taken not to exceed these temperatures in healthy tissue.

Systems and methods developed to control heating and prevent elevated temperatures to surrounding tissue typically include cooling fluid that circulates around at least a portion of the microwave energy delivery device. For example, in one system cooling fluid is provided to the distal end of the microwave energy delivery device via a thin-walled tube. The thin-walled tube deposits the cooling fluid near the microwave antenna and the cooling fluid flows proximally through a return path in the microwave energy deliver device.

There are several challenges to providing cooling to a microwave energy delivery device. The first challenge is providing suitable supply and return fluid pathways in the microwave energy delivery device without increasing the overall diameter of the microwave energy delivery device. Another challenge is providing suitable supply and return fluid pathways while maintaining a concentric configuration throughout the microwave energy delivery device. Yet another challenge is providing a suitable configuration that simplifies assembly and manufacturing.

SUMMARY

The microwave energy delivery devices described hereinbelow includes an assembly that forms a fluid-cooled device with a substantially concentric geometry along the length of the device without increasing in the overall diameter of the microwave energy delivery device.

An apparatus and method of fabricating a microwave energy delivery device, which is structurally robust enough for unaided direct insertion into tissue is described herein. The microwave antenna is generally comprised of a radiating portion which may be connected to a feedline (or shaft), which in turn, may be connected by a cable to a power generating source such as a generator. The microwave assembly may be a monopole microwave energy delivery device but is preferably a dipole assembly. The distal portion of the radiating portion preferably has a tapered end which terminates at a tip to allow for the direct insertion into tissue with minimal resistance. The proximal portion is located proximally of the distal portion.

The adequate rigidity necessary for unaided direct insertion of the antenna assembly into tissue, e.g., percutaneously, while maintaining a minimal wall thickness of less than 0.010 inches of an outer jacket, comes in part by a variety of different designs. An embodiment of a microwave design includes a coaxial cable. The coaxial cable includes an inner conductor, an outer conductor, and a dielectric insulator disposed therebetween. The radiating section includes a dipole antenna that is coupled to the feedline and a trocar coupled to the dipole antenna at a distal end thereof. The microwave antenna further includes an inflow hypotube disposed around the outer conductor. The inflow hypotube supplies fluid to the radiating portion. The inflow hypotube enables the increased in strength thereby allowing for a smaller wall thickness requirement of the outer jacket of a microwave antenna.

In one embodiment, the microwave antenna includes a feedline, a radiating section, an inflow hypotube, a puck, a transition collar and a sleeve. The feedline includes a coaxial cable with an inner conductor, an outer conductor, and a dielectric disposed therebetween. The radiating section includes a dipole antenna coupled to the feedline and a trocar coupled to the distal end of the dipole antenna. The inflow hypotube is disposed around the outer conductor and configured to supply fluid to the radiating portion. The puck includes two or more ribs extending from the first end to the second end. The ribs define inflow slots between two adjacent ribs. The transition collar is coupled to the distal end of the inflow hypotube and the puck includes at least two outflow slots at the proximal end. The transition collar is configured to receive fluid from a distal end of the inflow hypotube and transition the fluid from the outflow slots to a distal end of the radiating section. The sleeve overlays the outflow slots of the transition collar, the puck and at least the distal portion of the radiating section. The sleeve forms a first fluid-tight seal with the transition collar, proximal the outflow slots, and defines a first gap for transitioning the fluid to exit the outflow slots of the transition collar to the distal end of the radiating section. The sleeve may be a polyimide sleeve.

The microwave antenna may further include an outer jacket that surrounds the proximal to distal end of the feedline and an outer hypotube. The outer jacket forms a fluid-tight seal with the trocar and/or the distal end of radiating section and defines a second gap for receiving fluid from the first gap. The outer hypotube surrounds the inflow hypotube at the proximal end of the feedline and defines a third gap positioned relative to the inflow hypotube. The outer hypotube includes one or more slots defined therein and forms a fluid-tight seal with the outer jacket proximal one or more slots. The one or more slots are configured to enable the fluid to flow proximally from the second gap into the third gap and through the microwave antenna.

In another embodiment, the inflow hypotube and/or the outer hypotube are made from stainless steel or from a non-metallic composite such as PolyMed® made by Polygon. The wall thickness of the outer hypotube and the inflow hypotube may be less than about 0.010 inches. The microwave antenna may further include a choke configured to partially surround a proximate portion of the feedline In yet another embodiment, the puck is injection molded during the manufacturing process to form a water-tight seal around the outer conductor. The transition collar may be press-fit over the inflow hypotube to form a fluid-tight seal therebetween.

In a further embodiment, the microwave antenna may included a connection hub with a cable connector coupled to the feedline, an inlet fluid port and an outlet fluid port defined therein and a bypass tube configured to transition fluid proximate the cable connector to the outlet fluid port. An inflow tube may be coupled to the inlet fluid port for supplying the fluid thereto and an outflow tube may be coupled to the outlet fluid port and in fluid communication with the inflow hypotube for withdrawing fluid therefrom.

A method for manufacturing a microwave antenna is also disclosed herein and may include the steps of: providing a feedline including a coaxial cable including an inner conductor, an outer conductor, and a dielectric disposed therebetween; coupling a radiating section to the distal end of the feedline, the radiating section including a dipole antenna; coupling a trocar to the distal end of the dipole antenna; disposing an inflow hypotube around the outer conductor, the inflow hypotube configured to supply fluid to the radiating section; disposing a puck around at least a portion of the radiating section having a distal end and a proximal end, the puck including two or more longitudinal ribs for providing mechanical strength to the microwave antenna, the two or more ribs extending from the distal end to the proximal end to define inflow slots between two adjacent ribs; disposing a transition collar between a distal end of the inflow hypotube and a proximal end of the puck, the transition collar including at least two outflow slots configured to receive fluid from a distal end of the inflow hypotube and transition the fluid from the at least two outflow slots to a distal end of the radiating section; and disposing a sleeve to overlay the at least two outflow slots of the transition collar, the puck and at least the distal portion of the radiating section, the sleeve forming a fluid-tight seal with the transition collar proximal the at least two outflow slots and defining a first gap for transitioning the fluid to exit the at least two outflow slots of the transition collar to the distal end of the radiating section.

The method for manufacture may further include the steps of: disposing an outer jacket radially outward of the distal end of the feedline, the outer jacket forming a fluid-tight seal with one of the trocar and a distal end of the radiating section, the outer jacket defining a second gap for receiving fluid from the first gap; and disposing an outer hypotube radially outward of the inflow hypotube and defining a third gap positioned relative to the inflow hypotube, the outer hypotube including at least one slot defined therein and forming a fluid-tight seal with the outer jacket proximal the at least one slot, the at least one slot configured to enable the fluid to flow proximally from the second gap into the third gap and through the microwave antenna.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described herein below with reference to the accompanying drawings. In the following description, well-known functions or constructions are not described in detail to avoid obscuring the present disclosure in unnecessary detail.

Figure 1:
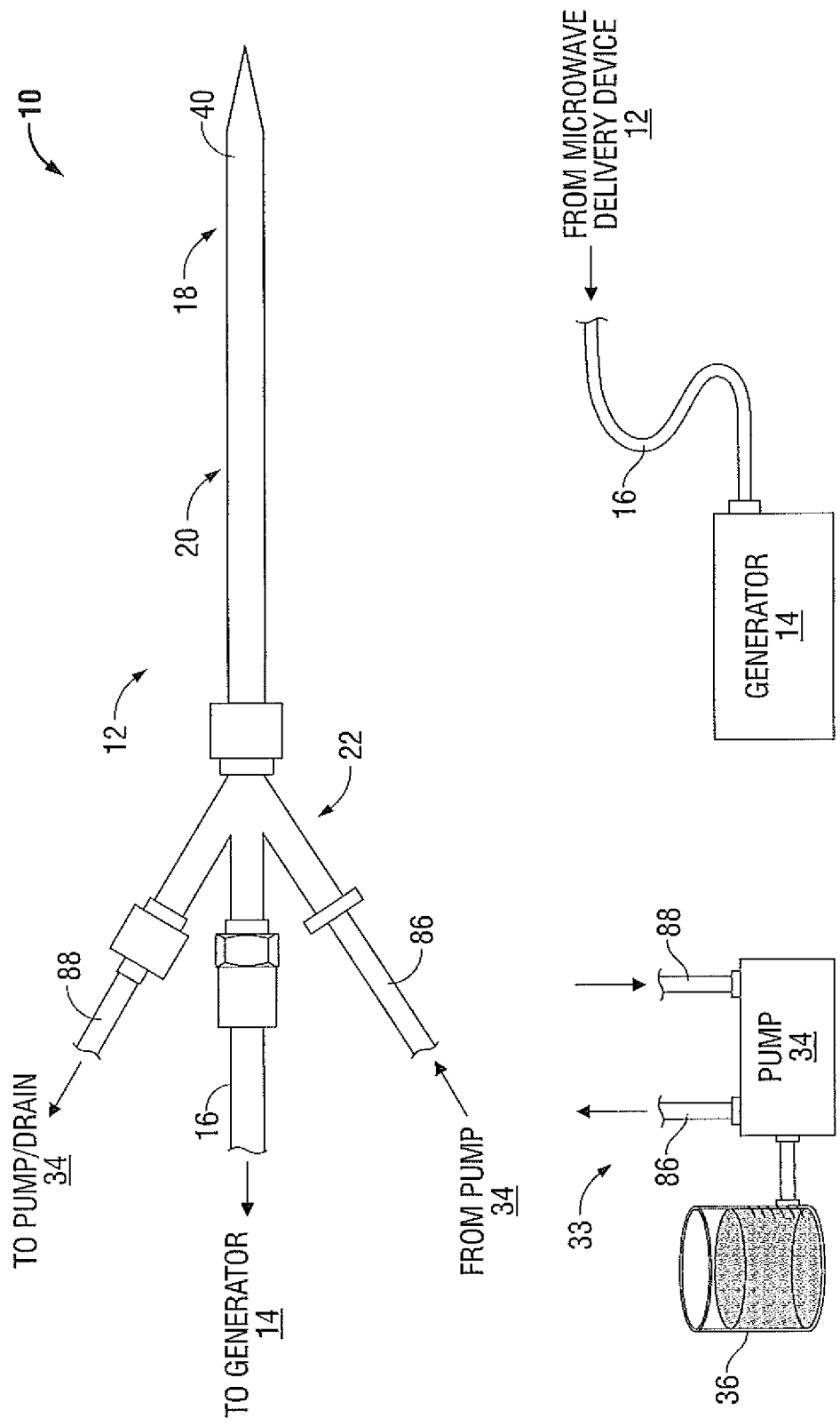
FIG. 1 is a schematic diagram of a microwave ablation system according to an embodiment of the present disclosure.

FIG. 1 illustrates a microwave ablation system 10 that includes a microwave energy delivery device 12, a microwave generator 14 and a cooling fluid supply 33. The microwave energy delivery device 12 is coupled to a microwave generator 14 via a flexible coaxial cable 16 and coupled to the cooling fluid supply 33 via cooling fluid supply lines 86 and 88. Cooling fluid exits the microwave energy delivery device 12 through a cooling fluid return line 88 and is discharged in a suitable drain. In a closed-loop cooling fluid system the microwave energy delivery device 12 couples to the cooling fluid supply 33 via a cooling fluid return line 88 and cooling fluid is cycled through the cooling fluid supply 33. In an opened-loop cooling fluid system the cooling fluid return line 88 deposits the cooling fluid in a drain or other suitable disposable receptacle and new cooling fluid is provided to the cooling fluids supply from a cooling fluid reservoir 36 or other suitable source of cooling fluid.

Microwave energy delivery device 12 generally includes a connection hub 22, a feedline 20 and a radiating portion 18. Connection hub 22 connects the microwave generator 14 and the cooling fluid supply 33 to the microwave energy delivery device 12. The microwave signal is produced by the microwave generator 14, transmitted through the flexible coaxial cable 16, which connects to the connection hub 22, and the connection hub 22 facilitates the transfer of the microwave energy signal to the feedline 20. Connection hub 22 further facilitates the transfer of cooling fluid to and from the feedline 20. Cooling fluid, provided from the pump 34 of the cooling fluid supply 33, is provided to the connection hub 22 through the cooling fluid supply line 86. Connection hub 22 transfers the cooling fluid from the cooling fluid supply line 86 to the cooling fluid supply lumen (not explicitly shown) of the feedline 20. Cooling fluid, after being circulated through the feedline 20 and radiating portion 18 of the microwave energy delivery device 12, is returned to the connection hub 22 through the return lumen (not explicitly shown) of the feedline 20. Connection hub 22 facilitates the transfer of the cooling fluid from the return lumen (not explicitly shown) to the cooling fluid return line 88.

In one embodiment, the microwave ablation system 10 includes a closed-loop cooling system wherein the cooling fluid return line 88 returns the cooling fluid to the pump 34 of the cooling fluid supply 33. The cooling fluid supply 33 cools the returned cooling fluid from the cooling fluid return line 88 before recirculating at least a portion of the returned cooling fluid through the Microwave ablation system 10.

In another embodiment, the cooling fluid return line 88 connects to a suitable drain and/or reservoir (e.g., cooling fluid from the microwave energy delivery device 12 is not returned to the cooling fluid supply 33). Cooling fluid reservoir 36 of the cooling fluid supply 33 provides a continuous supply of cooling fluid to the pump 34. Cooling fluid reservoir 36 may also include a temperature control system configured to maintain the cooling fluid at a predetermined temperature. Coolant fluid may include any suitable liquid or gas, including air, or any combination thereof.

The microwave energy delivery device 12 may include any suitable microwave antenna 40 such as, for example, a dipole antenna, a monopole antenna and/or a helical antenna. The microwave generator 14 may be configured to provide any suitable microwave energy signal within an operational frequency from about 300 MHz to about 10 GHz. The physical length of the microwave antenna 40 is dependant on the frequency of the microwave energy signal generated by the microwave generator 14. For example, in one embodiment, a microwave generator 14 providing a microwave energy signal at about 915 MHz drives a microwave energy delivery device 12 that includes a microwave antenna 40 with a physical length of about 1.6 cm to about 4.0 cm.

Figure 2:
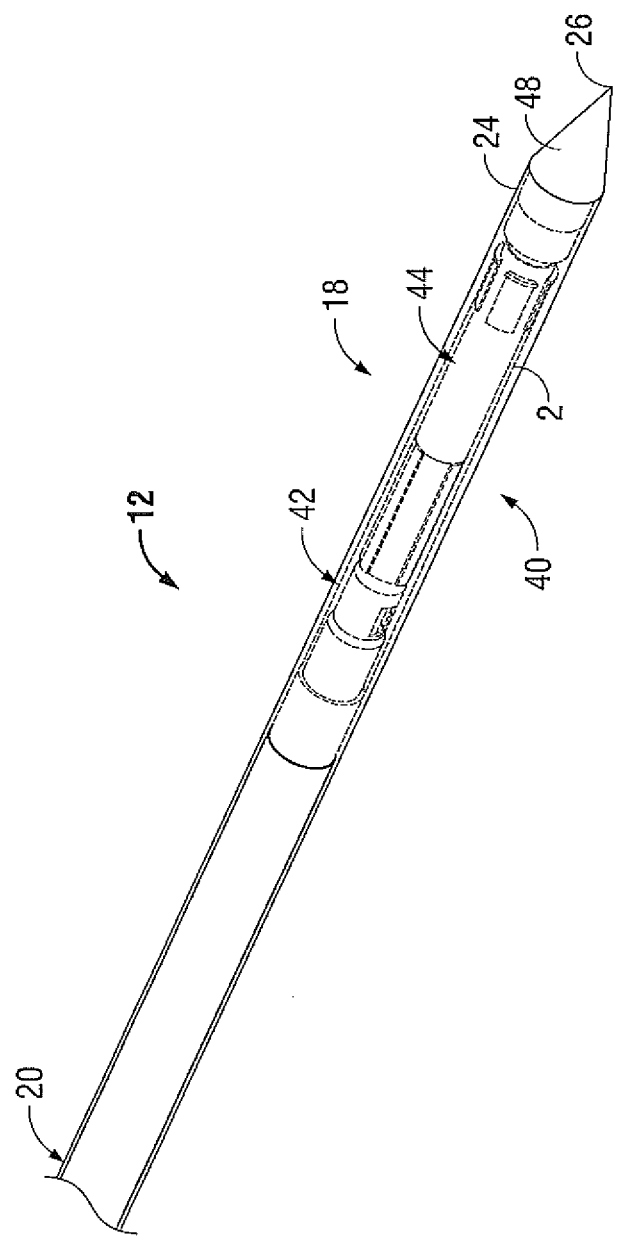
FIG. 2 is an isometric view of a distal portion of the microwave energy delivery device according to one embodiment of the present disclosure.

FIG. 2 is an enlarged view of the distal portion of the microwave energy delivery device 12 of FIG. 1 and includes a feedline 20, a proximal radiating portion 42 and a distal radiating portion 44. The proximal radiating portion 42 and the distal radiating portion 44 form a dipole microwave antenna 40. As illustrated in FIG. 2, proximal radiating portion 42 and the distal radiating portion 44 are unequal thereby forming an unbalanced dipole antenna 40. The microwave energy delivery device 12 includes a sharpened tip 48 having a tapered end 24 that terminates, in one embodiment, at a pointed end 26 to allow for insertion into tissue with minimal resistance at a distal end of the radiating portion 18. In another embodiment the radiating portion 18 is inserted into a pre-existing opening or catheter and the tip may be rounded or flat.

Sharpened tip 48 may be machined from various stock rods to obtain a desired shape. The sharpened tip 48 may be attached to the distal radiating portion 44 using various adhesives or bonding agents, such as an epoxy sealant. If the sharpened tip 48 is metal, the sharpened tip 48 may be soldered to the distal radiating portion 44 and may radiate electrosurgical energy. In another embodiment, the sharpened tip 48 and a distal radiating portion 44 may be machined as one piece. The sharpened tip 48 may be formed from a variety of heat-resistant materials suitable for penetrating tissue, such as ceramic, metals (e.g., stainless steel) and various thermoplastic materials, such as polyetherimide, polyimide thermoplastic resins, an example of which is Ultem® sold by General Electric Co. of Fairfield, Conn.

Figure 3A:
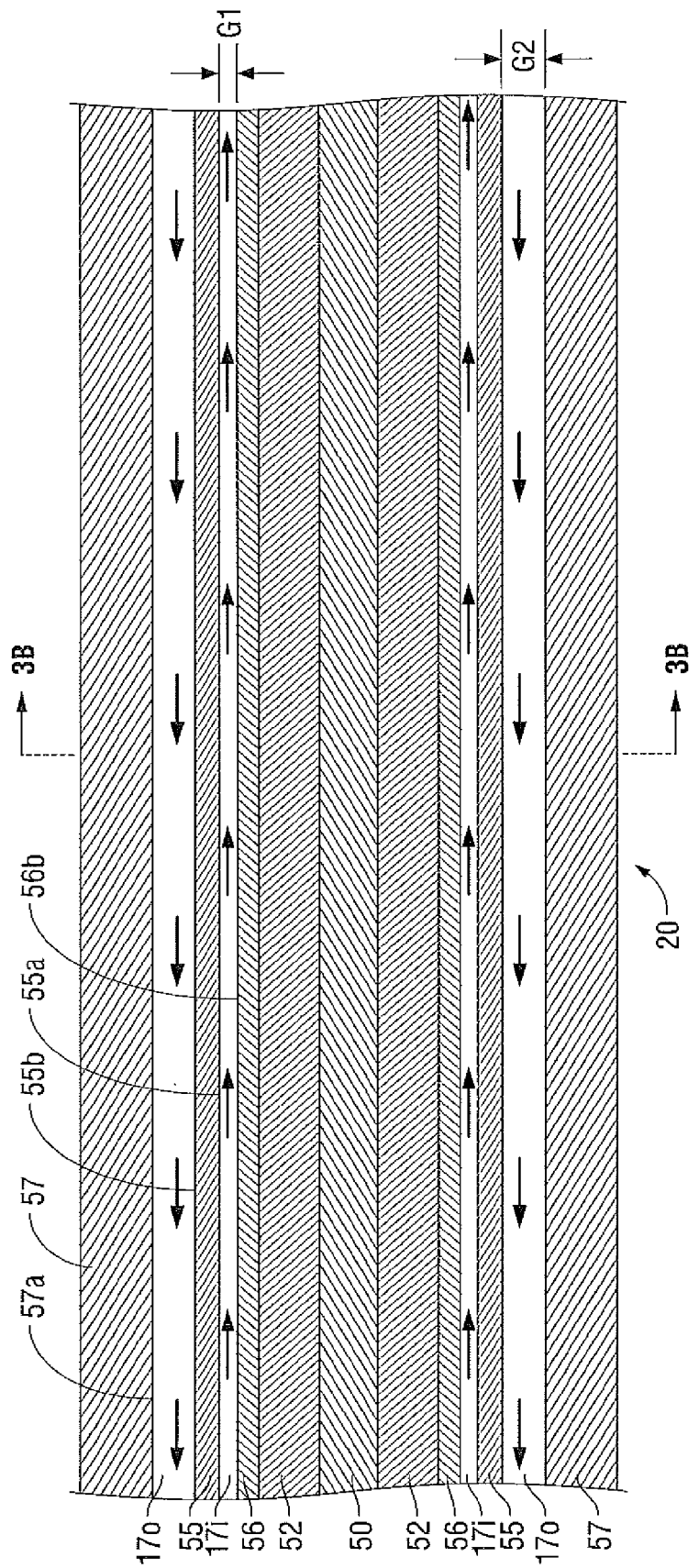
FIG. 3A is a longitudinal cross-sectional view of the feedline portion of the microwave energy delivery device of FIG. 2.
Figure 3B:
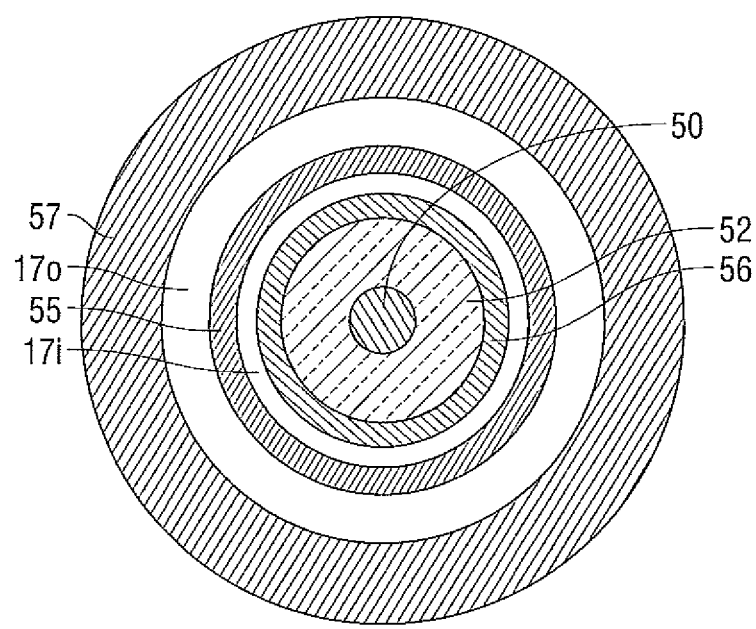
FIG. 3B is a traverse, cross-sectional view taken along line 3B-3B of FIG. 2.

FIG. 3A is a longitudinal cross-sectional view of a section of the feedline 20 of the microwave energy delivery device 12 of FIG. 1 and FIG. 3B is a transverse, cross-sectional view of the feedline 20 of the microwave energy delivery device 12 of FIG. 3A. Feedline 20 is coaxially formed with an inner conductor 50 at the radial center surrounded by a dielectric layer 52 and an outer conductor 56. Inflow hypotube 55 is spaced apart and disposed radially outward from the outer conductor 56. The outer surface of the outer conductor 56b and the inner surface of the inflow hypotube 55a form an inflow channel 17i allowing cooling fluid to flow distally through the feedline 20 of the microwave energy delivery device 12 as indicated by cooling fluid inflow arrows 17i. The inflow hypotube 55 may be formed from a variety of heat-resistant materials, such as ceramic, metals (e.g., stainless steel), various thermoplastic materials, such as polyetherimide, polyimide thermoplastic resins, an example of which is Ultem® sold by General Electric Co. of Fairfield, Conn., or composite medical tubing, an example of which is PolyMed sold by Polygon of Walkerton, Ind. In one embodiment, the inflow hypotube 55 may have a wall thickness less than about 0.010 inches. In another embodiment, the inflow hypotube 55 may have a wall thickness less than about 0.001 inches.

The outer hypotube 57 is spaced apart from, and radially outward from, the inflow hypotube 55. The outer surface of the inflow hypotube 55b and the inner surface of the outer hypotube 57a form an outflow channel 17o that allows cooling fluid to flow proximately through the feedline 20 of the microwave energy delivery device 12 as indicated by cooling fluid outflow arrows 17o. The outer hypotube 57 may be formed from a variety of heat-resistant materials, such as ceramic, metals (e.g., stainless steel), various thermoplastic materials, such as polyetherimide, polyimide thermoplastic resins, an example of which is Ultem® sold by General Electric Co. of Fairfield, Conn., or composite medical tubing, an example of which is PolyMed sold by Polygon of Walkerton, Ind. In one embodiment, the outer hypotube 57 may have a wall thickness less than about 0.010 inches. In another embodiment, the outer hypotube 57 may have a wall thickness less than about 0.001 inches.

The substantially radially concentric cross-sectional profile, as illustrated in FIG. 3B, provides uniform flow of fluid in both the inflow channel 17i and the outflow channel 17o. For example, an inflow channel gap G1 defined between the outer surface of the outer conductor 56b and the inner surface of the inflow hypotube 55a is substantially uniform around the circumference of the outer conductor 56. Similarly, an outflow channel gap G2 defined between the outer surface of the inflow hypotube 55b and the inner surface of the outer hypotube 57 is substantially uniform around the circumference of the inflow hypotube 55.

In addition, the cross-sectional area of the inflow channel 17i and the outflow channel 17o (i.e., the effective area of each channel in which fluid flows) is the difference between the area at the outer surface of each channels 17i, 17o (i.e., the area at the inner diameter of the inflow hypotube 55 and the area at the inner diameter of the outer hypotube 57, respectively) and the area at the inner surface of the each channels 17i, 17o (i.e., the area at the outer diameter of the outer conductor 56 and the area at the outer diameter of the inflow hypotube 55). The cross-sectional area of the inflow channel 17i and the outflow channel 17o is substantially uniform along the longitudinal length of the feedline 20. In addition, transverse shifting of the inflow hypotube 55 within the outer hypotube 57 or transverse shifting of the outer conductor 56 within the inflow hypotube 55, may create a non-uniform inflow or outflow channel gap G1, G2, but will not affect the cross-sectional area of either inflow channel 17i and/or outflow channel 17o.

Figure 4:
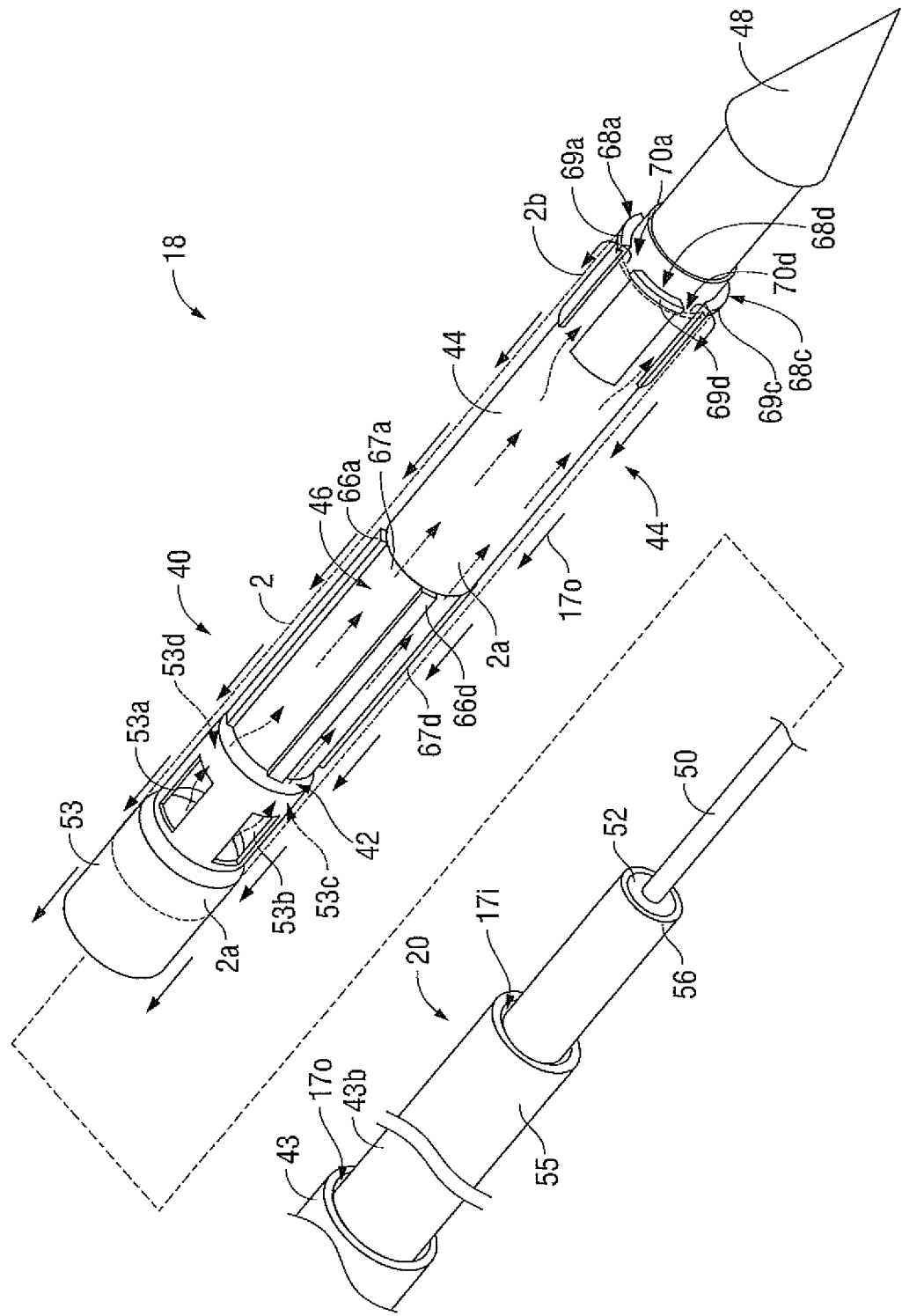
FIG. 4 is a perspective view of the distal portion of the microwave energy delivery device illustrating the coaxial inflow and outflow channels according to the present disclosure.

FIG. 4 (illustrating in partial assembly the radiating portion 18 of FIG. 1) further illustrates the inflow fluid flow pathways. The radiating portion 18 is formed by inserting the distal portion of the feedline 20 into the microwave antenna 40.

The feedline 20 is configured to provide cooling fluid and a microwave energy signal to the microwave antenna 40. As discussed hereinabove, the feedline 20 provides cooling fluid through the inflow channel 17i formed between the inflow hypotube 55 and the outer conductor 56 of the feedline 20. The feedline 20 also provides a microwave energy signal between the inner conductor 50 and the outer conductor 56.

The microwave antenna 40 includes a tapered inflow transition collar 53, a channeled puck 46, a distal radiating portion 44, including a plurality of antenna sleeve stops 68a-68d, and a sharpened tip 48. The feedline 20, when inserted into the microwave antenna 40, connects the outer conductor 56 to the tapered inflow transition collar 53 and the inner conductor 50 to the distal radiating portion 44.

Figure 5:
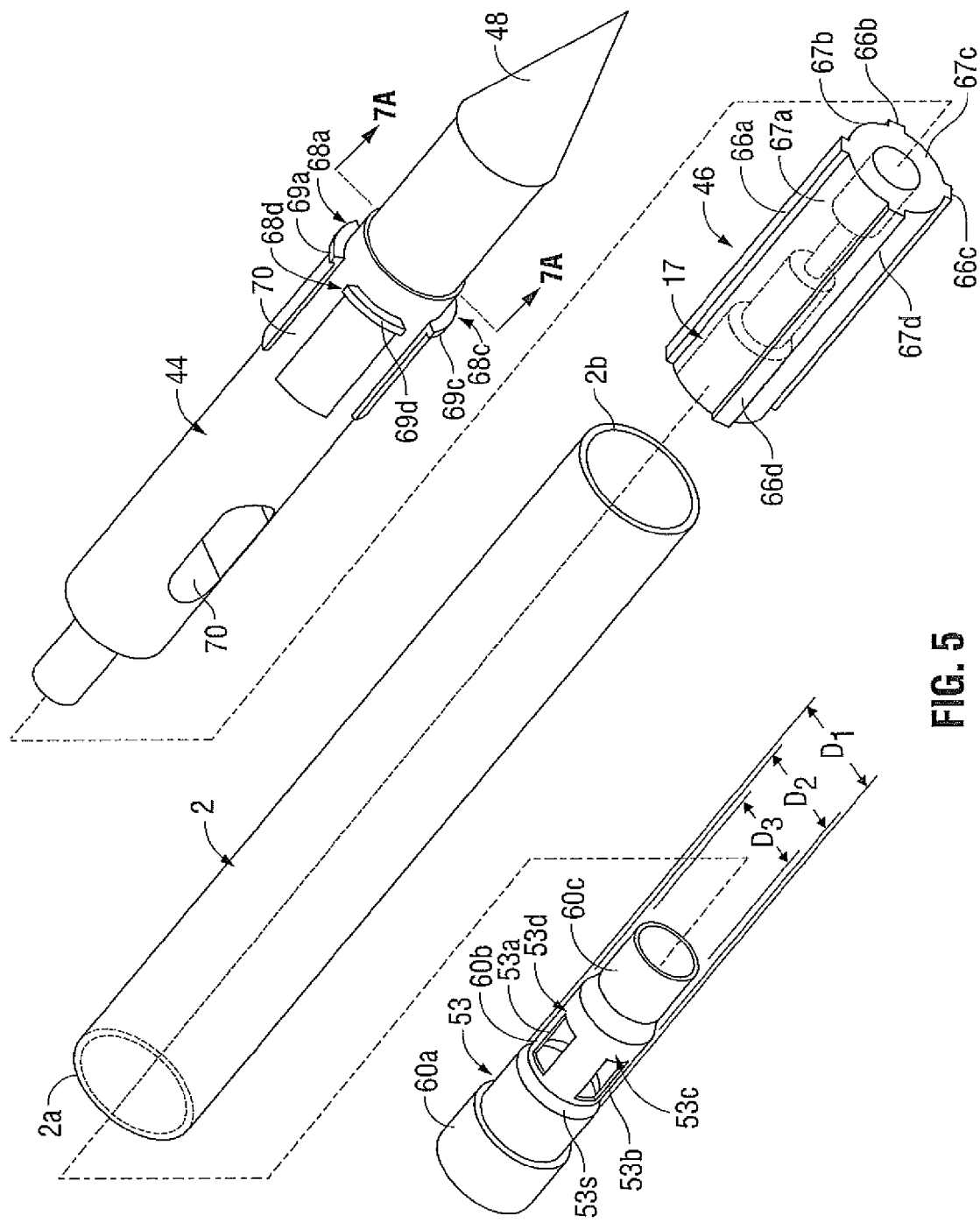
FIG. 5 is an exploded view of the distal portion of the microwave energy delivery device illustrated in FIG. 4.

FIG. 5 is an exploded view of the microwave antenna 40 of FIG. 4 that further illustrates the components of the microwave assembly. The tapered inflow transition collar 53 includes an outer taper 60a, a middle taper 60b and an inner taper 60c and is configured to transition the cooling fluid from the inflow channel 17i to various fluid channels formed in the microwave antenna 40 as discussed hereinbelow. During assembly, and as illustrated in FIG. 4 and discussed hereinbelow, the distal end of the feedline 20 is inserted into the proximal end of the tapered inflow transition collar 53. Each component 50, 52, 55, 56 of the feedline 20 is cut to a specific length such that when the feedline 20 is inserted each component ends at a predetermined position within the microwave antenna assembly 40.

Starting with the radially-outward component of the distal end of the feedline 20, the inflow hypotube 55 (See FIG. 4) is inserted into the proximal end of the outer taper 60a portion of the tapered inflow transition collar 53. The transition between the outer taper 60a and the middle taper 60b forms a mechanical stop for the inflow hypotube 55. Outer taper 60a and inflow hypotube 55 forms a fluid-tight seal therebetween thereby limiting cooling fluid to the middle taper 60b of the tapered inflow transition collar 53. The fluid-tight seal between the inflow hypotube 55 and the outer taper 60a may be formed by adhesive, epoxy, or a polytetrafluoroethylene or other suitable sealant, or fluid-tight seal may be formed by a tight mechanical connection between the inflow hypotube 55 and the outer taper 60a.

In one embodiment, the inflow hypotube 55 is formed of a conductive metal such as, for example, stainless steel, steel, copper or any other suitable metal, and the fluid-tight seal insulates the inflow hypotube 55 and the inner surface of the tapered inflow transition collar 53. In another embodiment, the fluid tight seal may include one or more insulating materials that forms a dielectric barrier between the inflow hypotube 55 and tapered inflow transition collar 53.

The outer conductor 56 when inserted into the proximal end of the outer taper 60a extends through the middle taper 60b with at least a portion of the outer conductor 56 connecting to the inner taper 60c. The outer conductor 56 and inner taper 60c form an electrical connection therebetween such that microwave energy signal provided by the outer conductor 56 conducts to the tapered inflow transition collar 53 such that the tapered inflow transition collar 53 forms at least a portion of the proximal radiating portion 42 of the microwave antenna 40.

The outer surface of the inflow hypotube 55 and the inner surface of the outer taper 60a form a fluid-tight seal therebetween, Fluid exits the inflow channel 17i and is deposited in the open area formed within the middle taper 60b. The outer surface of the outer conductor 56 and inner surface of the inner taper 60c form a fluid-tight seal therebetween, thereby preventing the cooling fluid from traveling distal of the middle taper 60b within the tapered inflow transition collar 53.

In one embodiment, an electrical connection is formed between the outer conductor 56 and the inner taper 60c of the tapered inflow transition collar 53. As such, tapered inflow transition collar 53 forms at least a portion of the proximal radiating portion 42 of the radiating portion 18, wherein the radiating portion 18 is a dipole antenna. The electrical connection between the outer conductor 56 and the inner taper 60c may include all of the contact surface therebetween or the electrical connection may include only a portion thereof. For example, in one embodiment the electrical connection between the outer conductor 56 and the inner taper 60c is formed circumferentially along the distal portion of the inner taper 60c and the remaining portion of the contact surface insulates the outer conductor 56 and the inner taper 60c.

In another embodiment, the fluid-tight seal between the outer conductor 56 and the inner taper 60c forms an insulating barrier therebetween and the tapered inflow transition collar 53 does not form a portion of the radiating portion 18, wherein the radiating portion 18 is a monopolar antenna.

In yet another embodiment, the fluid-tight seal between the outer conductor 56 and the inner taper 60c forms an insulating barrier therebetween. An electrical connection between the outer conductor 56 and the inner taper 60e is formed by connecting a distal end of the outer conductor 56 or the inner taper 60e to one another.

The fluid-tight seal between the inflow hypotube 55 and the outer taper 60a and the fluid-tight seal between the outer conductor 56 and the inner taper 60c isolates the cooling fluid discharged from the inflow channel 17i to the middle taper 60b of the tapered inflow transition collar 53. As additional fluid is deposited in the middle taper 60b, pressure builds and the cooling fluid exits the middle taper 60b through one of the plurality of cooling fluid transition apertures 53a-53d formed in the tapered inflow transition collar 53.

After the cooling fluid flows radially outward through one of the plurality of cooling fluid transition apertures 53a-53d formed in the middle taper 60b, the cooling fluid flows distally along the outer surface of the middle taper 60b between the tapered inflow transition collar 53 and the antenna sleeve 2. Antenna sleeve 2 forms a fluid-tight seal with the outer taper 60a of the tapered inflow transition collar 53 thereby requiring fluid to flow distally toward the channeled puck 46. In one embodiment, the antenna sleeve 2 is a thin polyimide sleeve, or other suitable non-conductive material that has little or no impact on the transmission and/or delivery of microwave radiation.

With reference to FIG. 4, cooling fluid exiting one of the plurality of cooling fluid transition apertures 53a-53d flows distally along the outer surface of the tapered inflow transition collar 53, the outer surface of the channeled puck 46 and the outer surface of the distal radiating portion 44 and along the inner surface of the antenna sleeve 2. Proximal end of antenna sleeve 2 forms a fluid-tight seal with the outer taper 60a of the tapered inflow transition collar 53. In one embodiment, the proximal end 2a of the antenna sleeve 2 mates with a proximal antenna sleeve stop 53s formed in the outer taper 60a such that the outer diameter of the antenna sleeve 2 and the outer diameter of the outer taper 60a are substantially identical.

A channel 67a, 67b, 67c, 67d is formed between each of the adjacent raised portions 66a-66d wherein the radial outer surface of the channeled puck 46 at the raised portion 66a-66d is radially outward from the outer surface of the channeled puck 46 at each of the channels 67a-67d. Channels 67a-67d are configured to form a cooling fluid pathway between the outer surface of the channeled puck 46 and the inner surface of the antenna sleeve 2.

As illustrated in FIG. 4, cooling fluid exits the middle taper 60b of the tapered inflow transition collar 53, flows distal through the plurality of channels 67a-67d formed between the raised portions 66a-66d of the channeled puck 46 and the antenna sleeve 2 and is deposited on the outer surface of the distal radiating portion 44. The cooling fluid is deposited into a gap formed between the outer surface of the proximal end 2a of the distal radiating portion 44 and the inner surface of the antenna sleeve 2.

Distal end 2b of the distal radiating portion 44 includes a plurality of antenna sleeve stops 68a-68d. Adjacent antenna sleeve stops 68a-68d are spaced apart from each other and form a plurality of distal flow channels 70a-70d therebetween. Distal end 2b of antenna sleeve 2 is configured to abut a distal lip 69a-69d formed on the distal end of each of the respective antenna sleeve stops 68a-68d.

Figure 6:
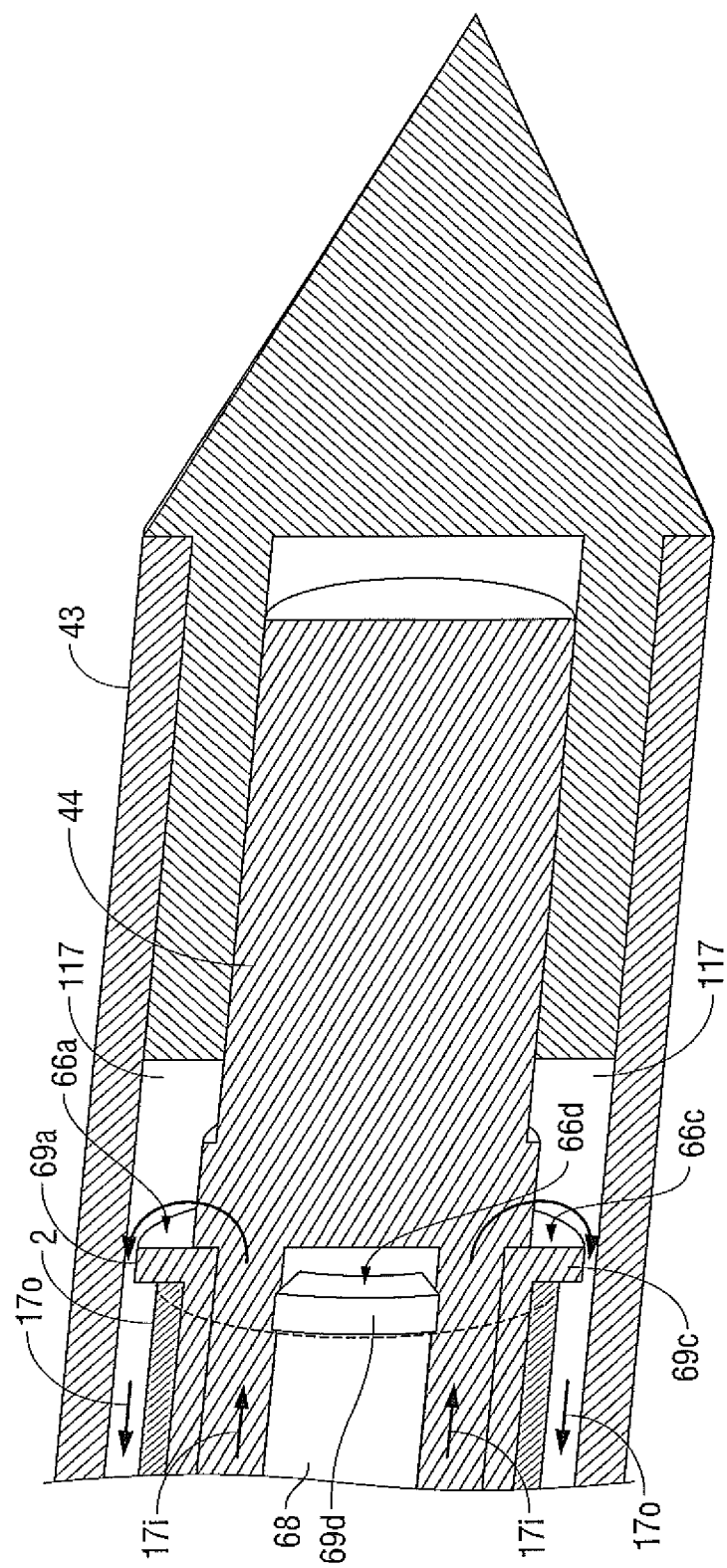
FIG. 6 is a longitudinal cross-sectional view of the distal tip of the microwave energy delivery device.

Fully assembled, the distal end of the outer jacket 43 forms a fluid tight seal with a proximal portion of the sharpened tip 48. As illustrated in FIG. 6, a fluid-tight seal is formed between the outer jacket 43 and the sharpened tip 48, wherein the fluid-tight seal is distal the distal end 2b of the antenna sleeve 2. As such, the antenna sleeve 2 is contained within the outer jacket 43 and at least a portion of the outflow channel 17o is formed between the inner surface of the outer jacket 43 and the outer surface of the antenna sleeve 2.

In one embodiment, the distal lip 69a-69d of the respective antenna sleeve stops 68a-68d extend radially outward from the outer surface of the antenna sleeve 2 and space the outer jacket 43 from the outer surface of the antenna sleeve 2. A gap is formed between the antenna sleeve 2 and the outer jacket 43 that forms at least a portion of the outflow channel 17o. The plurality of circumferentially-spaced sleeve stops 68a-68d uniformly position the outer jacket 43 with respect to the antenna sleeve 2.

FIG. 5 is an exploded view of a portion of the radiating portion 18 illustrated in FIG. 4 including the tapered inflow transition collar 53, the channeled puck 46, the distal radiating portion 44, the antenna sleeve 2 and the sharpened tip 48. Assembled, the channeled puck 46 is positioned between the tapered inflow transition collar 53 and the distal radiating portion 44. Similarly, the antenna sleeve 2 is also positioned between a portion of the tapered inflow transition collar 53 and the distal radiating portion 44; the antenna sleeve 2 being spaced radially outward from the channeled puck 46.

As discussed hereinabove, the tapered inflow transition collar 53 includes an outer taper 60a, a middle taper 60b and an inner taper 60c. A portion of the outer surface of the outer taper 60a may form a proximal antenna sleeve stop 53s configured to receive the proximal end of the antenna sleeve 2. Outer taper 60a is configured to slide over the distal end of the inflow hypotube 55. Inflow hypotube 55 may abut the transition portion between the outer taper 60a and the middle taper 60b. Fluid-tight seals, formed between the inflow hypotube 55 and the outer taper 60a and between the outer conductor 56 and the inner taper 60c, force the cooling fluid traveling distally through in inflow channel 17i (formed between outer surface of the outer conductor 56 and the inner surface of the inflow hypotube 55, see FIG. 3A) to be deposited into the middle taper 60b of the tapered inflow transition collar 53.

Figure 8:
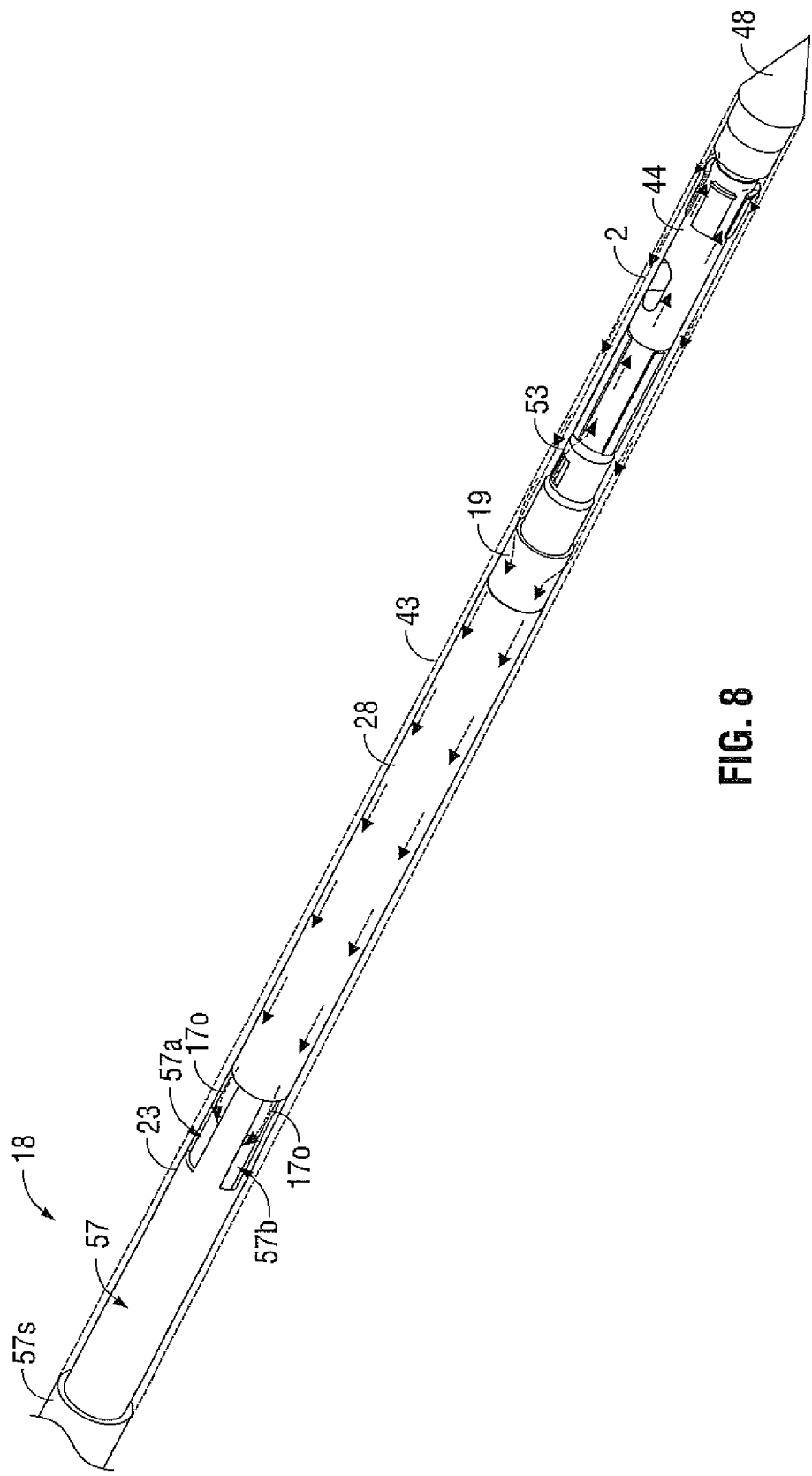
FIG. 8 is a perspective view of the distal portion of the microwave energy delivery device illustrating the coaxial outflow channel according to the present disclosure.

In one embodiment the fluid-tight seal between the tapered inflow transition collar 53 and the inflow hypotube 55 is formed by a press-fit connection therebetween. The inflow hypotube 55 may be press-fit over the tapered inflow transition collar 53 or the tapered inflow transition collar 53 may be press-fit over the inflow hypotube 55, as illustrated in FIGS. 2, 4 and 8.

The outer diameters of the outer taper 60a, a middle taper 60b and an inner taper 60c, D1, D2, D3, respectively, and the thickness of each taper 60a-60c are configured to facilitate the assembly of components that form the microwave energy delivery device 12. For example, the diameter D1 and thickness of the outer taper 60a is selected such that the inflow hypotube 55 forms a fluid-tight seal with the inner surface of the outer taper 60a and the antenna sleeve 2 forms a fluid-tight seal with the outer diameter of the outer taper 60a. The diameter D2 of the middle taper 60b is selected to provide an adequate gap between the outer conductor 56 and the antenna sleeve 2 and to facilitate fluid flow through the middle taper 60b. The diameter D3 and thickness of the inner taper 60c is selected such that the outer conductor 56 forms a fluid tight seal with the inner surface of the inner taper 60c and the channeled puck 46 forms a fluid-tight seal with the outer diameter of the inner taper 60c.

The three tiers of the tapered inflow transition collar 53 are configured to facilitate the transition of cooling fluid between a first portion of the inflow channel 17i (radially formed in a first portion of the coaxially configured structure) and a second channel portion of the inflow channel 17i (radially formed in a second portion of the coaxially configured structure). For example (proximal to the tapered inflow transition collar 53), a first portion of the inflow channel 17i is formed between the outer surface of the outer conductor 56 and the inner surface of the inflow hypotube 55 and at a point distal to the tapered inflow transition collar 53, a second portion of the inflow channel 17i is formed between the antenna sleeve 2 and the channeled puck 46.

In another embodiment, the tapered inflow transition collar 53 facilitates the transition of fluid from a first portion of the inflow channel 17*i* formed at a first radial distance from the radial center of the microwave energy delivery device 12 to a second portion of the inflow channel 17*i* formed at a second radial distance from the radial center of the microwave energy delivery device 12. The first and second radial distances from the radial center of the microwave energy delivery device 12 may or may not be equal.

The proximal end of the channeled puck 46 is configured to receive at least a portion of the inner taper 60*c* of the tapered inflow transition collar 53 and forms a fluid-tight seal therebetween and the distal end of the channeled puck 46 is configured to receive at least a portion of the distal radiating portion 44. The inner conductor (not explicitly shown) extends through the radial center of the channeled puck 46 and is received by the distal radiating portion 44.

In one embodiment the channeled puck 46 is injection molded during the manufacturing process to form a water-tight seal around a portion of the outer conductor 56 and/or a portion of the tapered inflow transition collar 53. In another embodiment, the channeled puck 46 is press-fit over a portion of the outer conductor and/or a portion of the tapered inflow transition collar 53 and forms a fluid-tight seal therebetween.

The distal radiating portion 44 includes a conductive member that may be formed from any type of conductive material, such as metals (e.g., copper, stainless steel, tin, and various alloys thereof). The distal radiating portion 44 may have a solid structure and may be formed from solid wire (e.g., 10 AWG). In another embodiment, the distal radiating portion 44 may be formed from a hollow sleeve of an outer conductor 56 of the coaxial cable or another cylindrical conductor. The cylindrical conductor may then be filled with solder to convert the cylinder into a solid shaft. More specifically, the solder may be heated to a temperature sufficient to liquefy the solder within the cylindrical conductor (e.g., 500° F.) thereby creating a solid shaft.

The radially-outward surface of the channeled puck 46 includes a plurality of raised portions 66*a*-66*d* and/or a plurality of recessed portions that form the channels 67*a*-67*d*. The plurality of raised portions 66*a*-66*d* are configured to slideably engage the antenna sleeve 2 and form a plurality of inflow channels 17*i* defined between the recessed portions and the inner surface of the antenna sleeve 2.

Antenna sleeve 2 is configured to surround the channeled puck 46 and surround at least a portion of the distal radiating portion 44. As discussed hereinabove, the proximal end portion of the antenna sleeve 2 connects to the proximal antenna sleeve stop 53*s* (formed in a portion of the outer taper 60*a*) and the distal end portion of the antenna sleeve 2 connects to the distal antenna sleeve stops 68*a*-68*d* formed in the distal radiating portion 44. A electrical connection between the distal radiating portion 44 and the inner conductor (not explicitly shown) may be formed through access slot 70. The access slot 70 may be filled with a suitable electrically conductive material and an electrical connection may be formed between the distal radiating portion 44 and the inner conductor (not explicitly shown). Distal end of the distal radiating portion 44 may connect to sharpened tip 48 or may form the sharpened tip 48.

The inflow channel 17*i* and the outflow channel 17*o* (i.e., the paths of the cooling fluid as it flows through the distal end of the microwave energy delivery device 12) are illustrated in FIGS. 4 and 6. Cooling fluid flows distally through the distal flow channels 70*a*-70*d* formed between adjacent antenna sleeve stops 68*a*-68*d*. After the cooling fluid flows distal of the distal end 2*b* of the antenna sleeve 2, the fluid is deposited in a fluid transition chamber 117 formed between the distal radiating portion 44 and the outer jacket 43. A fluid-tight seal, framed between the outer jacket 43 and the sharpened tip 48, prevents fluid from flowing distal the fluid transition chamber 117. As indicated by the transition arrows cooling fluid in the fluid transition chamber 117 exits the fluid transition chamber 117 and flows proximally and into the outflow channel 17*o* formed between the outer surface of the antenna sleeve 2 and the inner surface of the outer jacket 43.

Figure 7A:
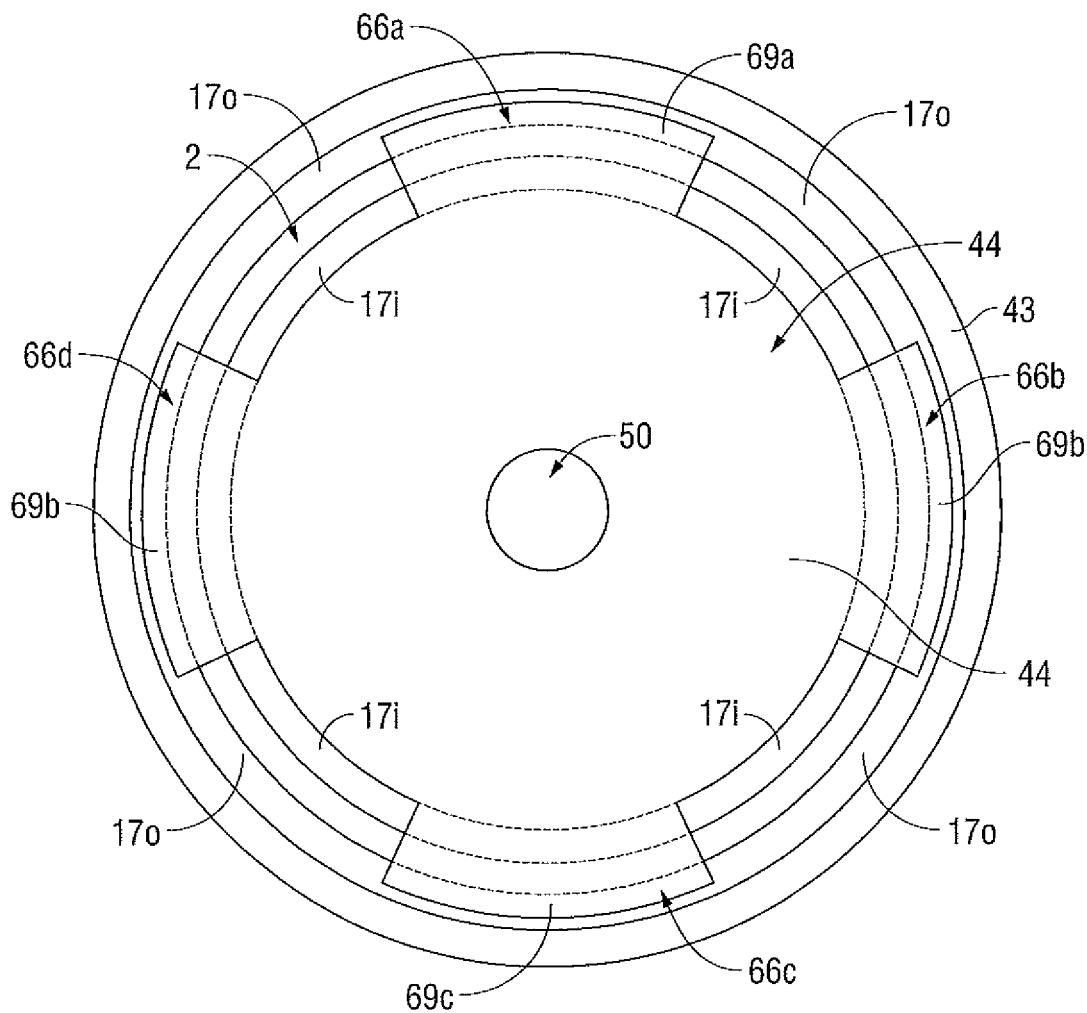
FIG. 7A is a transverse, cross-sectional view of the distal tip of the microwave energy delivery device according to one embodiment of the present disclosure.
Figure 7B:
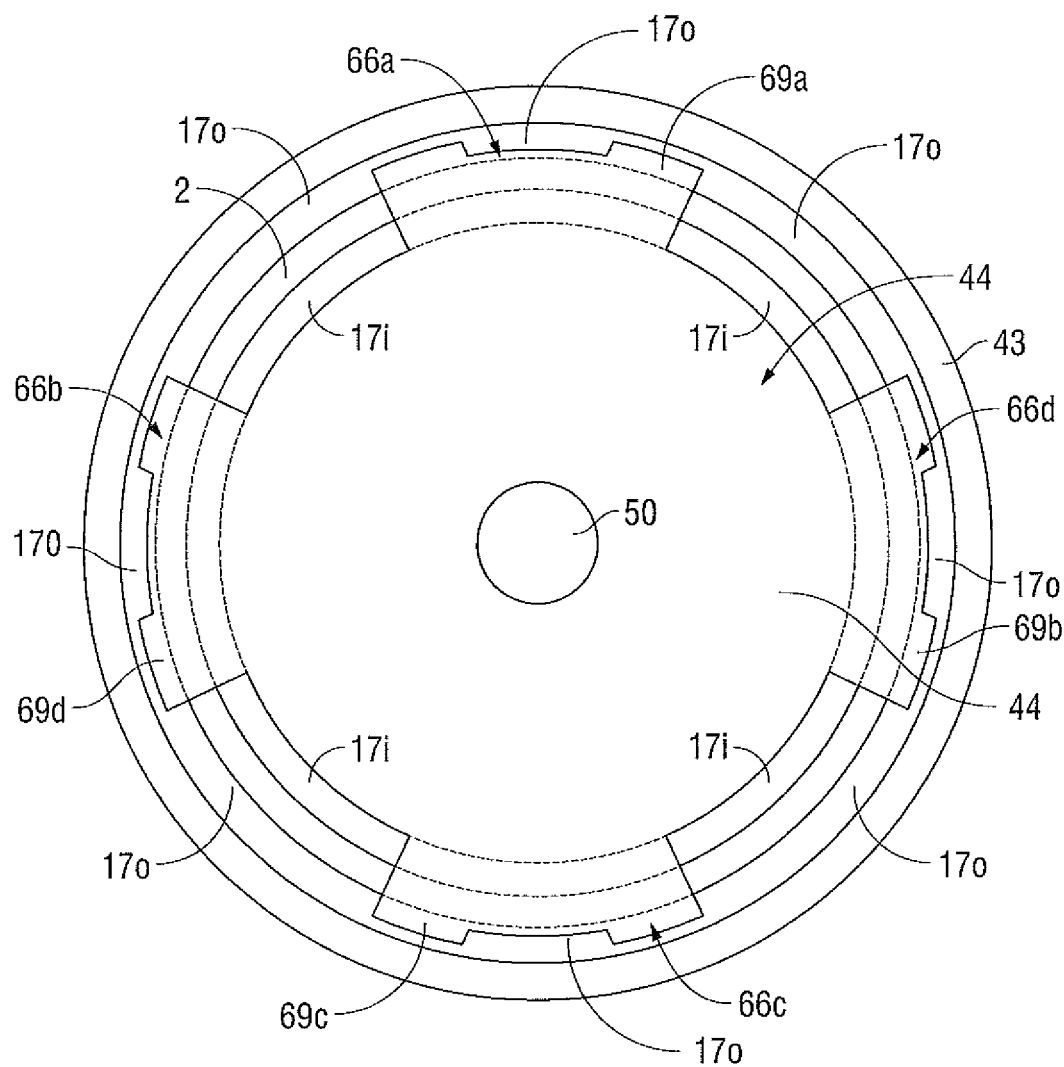
FIG. 7B is a transverse, cross-sectional view of the distal tip of the microwave energy delivery device according to another embodiment of the present disclosure.

In another embodiment and as illustrated in FIGS. 7A-7B, the radially outward portion of the distal lip 69*a*-69*d* formed on the distal end of each of the respective antenna sleeve stops 68*a*-68*d* (i.e., the portion of the distal lips 69*a*-69*d* that contact the outer jacket 43) may form additional channels between the distal lips 69*a*-69*d* and the outer jacket 43 to allow the cooling fluid to flow proximally from the fluid transition chamber 117.

The distal portion of the outflow channel 17*o* is illustrated in FIG. 8. The outer jacket 43 forms the outer boundary of the outflow channel 17*o* in the distal portion of the microwave energy delivery device 12. The distal end of the outer jacket 43 forms a fluid tight seal with the sharpened tip 48 and/or the distal radiating portion 44 and the proximal end forms a fluid tight seal with a portion of the outer hypotube 57 proximal the fluid outflow slots 57*a*, 57*b* (57*c*, 57*d* not shown). Outer hypotube 57 may further include a proximal outer jacket stop 57*s* that provides a smooth transition on the outer surface of the microwave energy delivery device 12 between the outer hypotube 57 and the outer jacket.

A portion of the outflow channel 17*o* is formed between the interior surface of the outer jacket 43 and at least a portion of the antenna sleeve 2, a portion of the tapered inflow transition collar 53, a portion of the choke dielectric 19, a portion of the EMF shield 28 that covers the core choke (not shown) and a portion of the outer hypotube 57. The coaxial arrangement of the outflow channel 17*o* provides for the uniform application of cooling fluid to the distal portion of the microwave energy delivery device 12.

On the proximal end of the outer jacket 43 the fluid-tight seal between the outer jacket 43 and the outer hypotube 57 directs the cooling fluid to travel through the fluid outflow slots 57*a*, 57*b* (57*c*, 57*d* not explicitly shown) and into the portion of the outflow channel 17*o* formed between the interior surface of the outer hypotube 57 and the outer surface of the inflow hypotube 55, as illustrated in FIG. 3A and described hereinabove.

As illustrated in FIGS. 1-8 and described hereinabove, the microwave energy delivery devices 12 includes a substantially coaxially arrangement through the length. Various layers of the microwave energy delivery device 12 form a substantially coaxial arrangement of the inflow channel 17*i* and a substantially coaxial arrangement of the outflow channel 17*o* between two (or more) of the coaxial layers. The substantially coaxial inflow and outflow channels 17*i*, 17*o* coaxially distribute the cooling fluid and thereby provides even cooling throughout the microwave energy delivery device 12.

Various structures in the microwave energy delivery device 12 facilitate the transition of the cooling fluid between the various sections of the inflow and outflow channels 17*i*, 17*o* respectively, while maintaining a substantially coaxial arrangement throughout the device. The tapered inflow transition collar 53 transitions the cooling fluid from inflow channel 17*i* formed between the outer conductor 56 and inflow hypotube 55 and an inflow channel 17*i* formed between the antenna sleeve 2 and the tapered inflow transition collar 53, the channeled puck 46 and the distal radiating portion 44. The distal flow channels 70*a*-70*d* formed by the arrangement of the antenna sleeve stops 68*a*-68*d* transition the cooling fluid from the inflow channel 17*i* formed between the antenna sleeve 2 and the distal radiating portion 44 to the outflow channel 17o formed between the outer surface of the antenna sleeve 2 and the inner surface of the outer jacket 43. Finally, the fluid outflow slots 57a-57d formed in the outer hypotube 57 directs the cooling fluid from outflow channel 17o formed between the EMF shield 28 and the outer jacket 43 and an outflow channel 17o formed between the inflow hypotube 55 and the outer hypotube 57. As such, the cooling fluid maintains a substantially coaxial arrangement along the length of the microwave energy delivery device 12.

Various structures of the microwave energy delivery device 12 facilitate the substantially coaxial fluid flow while supporting the coaxial arrangement. For example, the raised portions 66a of the channeled puck 46, the outer taper 60a of the tapered inflow transition collar 53 and the distal portions of the antenna sleeve stops 68a-68d position the antenna sleeve 2 in substantially coaxial arrangement while forming a portion of the inflow channel 17i therebetween. Similarly, the sharpened tip 48, the distal portions of the antenna sleeve stops 68a-68d and the inflow hypotube 55 position the outer jacket 43 in substantially coaxial arrangement while forming a portion of the outflow channel 17o therebetween.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A microwave antenna, comprising:
    a feedline including a coaxial cable including an inner conductor, an outer conductor, and a dielectric disposed therebetween;
    a radiating section including a dipole antenna coupled to the feedline and a trocar coupled to the dipole antenna at a distal end thereof;
    an inflow hypotube disposed around the outer conductor, the inflow hypotube configured to supply fluid to the radiation section;
    a puck having a first end and a second end, the puck including at least two ribs extending from the first end to the second end defining inflow slots between two adjacent ribs;
    a transition collar having a first end and a second end, the first end coupled to a distal end of the inflow hypotube and the second end coupled to the first end of the puck, the transition collar including at least two outflow slots at a proximal end thereof configured to receive fluid from the distal end of the inflow hypotube and transition the fluid from the at least two outflow slots to a distal end of the radiating section, the transition collar being press-fit over the inflow hypotube and forming a fluid-tight seal therebetween; and
    a sleeve overlaying the at least two outflow slots of the transition collar, the puck and at least the distal portion of the radiating section, the sleeve forming a first fluid-tight seal with the first end of the transition collar proximal the at least two outflow slots, the sleeve defining a first gap for transitioning the fluid to exit the at least two outflow slots of the transition collar to the distal end of the radiating section.

2. The microwave antenna according to claim 1, further comprising:
    an outer jacket surrounding the proximal to distal end of the feedline and forming a fluid-tight seal with one of the trocar and the distal end of the radiating section, the outer jacket defining a second gap for receiving fluid from the first gap; and
    an outer hypotube surrounding the inflow hypotube at the proximal end of the feedline and defining a third gap positioned relative to the inflow hypotube, the outer hypotube including at least one slot defined therein, the outer hypotube forming a fluid-tight seal with the outer jacket proximal the at least one slot, the at least one slot configured to enable the fluid to flow proximally from the second gap into the third gap and through the microwave antenna.

3. The microwave antenna according to claim 2, wherein the inflow hypotube and the outer hypotube are made from stainless steel.

4. The microwave antenna according to claim 2, further including a choke configured to at least partially surround a proximate portion of the feedline.

5. The microwave antenna according to claim 2, wherein the outer jacket is a non-metallic composite thin-walled outer jacket.

6. The microwave antenna according to claim 2, wherein the outer jacket has a wall thickness less than 0.010 inches.

7. The microwave antenna according to claim 2, wherein the puck is formed by injection molding to form a water-tight seal around the outer conductor.

8. The microwave antenna according to claim 2, further including a connection hub, the connection hub including:
    a cable connector coupled to the feedline;
    an inlet fluid port and an outlet fluid port defined therein; and
    a bypass tube configured to transition fluid proximate the cable connector to the outlet fluid port.

9. The microwave antenna according to claim 8, further including:
    at least one inflow tube coupled to the inlet fluid port for supplying the fluid thereto; and
    at least one outflow tube coupled to the outlet fluid port and in fluid communication with the at least one inflow hypotube for withdrawing fluid therefrom.

10. The microwave antenna according to claim 1, wherein the sleeve is a polyimide sleeve.

11. A method for manufacturing a microwave antenna, comprising:
    providing a feedline including a coaxial cable including an inner conductor, an outer conductor, and a dielectric disposed therebetween, the feedline having a distal end and a proximal end;
    coupling a radiating section to the distal end of the feedline, the radiating section including a dipole antenna;
    coupling a trocar to a distal end of the dipole antenna;
    disposing an inflow hypotube around the outer conductor, the inflow hypotube configured to supply fluid to the radiating section;
    disposing a puck around at least a portion of the radiating section having a distal end and a proximal end, the puck including at least two longitudinal ribs for providing mechanical strength to the microwave antenna, the at least two ribs extending from the distal end to the proximal end defining inflow slots between two adjacent ribs;
    disposing a transition collar between a distal end of the inflow hypotube and the proximal end of the puck, the transition collar including at least two outflow slots configured to receive fluid from the distal end of the inflow hypotube and transition the fluid from the at least two outflow slots to a distal end of the radiating section, the transition collar being press-fit over the inflow hypotube; and disposing a sleeve to overlay the at least two outflow slots of the transition collar, the puck and at least a distal portion of the radiating section, the sleeve forming a fluid-tight seal with the transition collar proximal the at least two outflow slots, the sleeve defining a first gap for transitioning the fluid to exit the at least two outflow slots of the transition collar to the distal end of the radiating section.

12. The method according to claim 11, further including the steps of:

disposing an outer jacket radially outward of the distal end of the feedline, the outer jacket forming a fluid-tight seal with one of the trocar and the distal end of the radiating section, the outer jacket defining a second gap for receiving fluid from the first gap; and disposing an outer hypotube radially outward of the inflow hypotube and defining a third gap positioned relative to the inflow hypotube, the outer hypotube including at least one slot defined therein, the outer hypotube forming a fluid-tight seal with the outer jacket proximal the at least one slot, the at least one slot configured to enable the fluid to flow proximally from the second gap into the third gap and through the microwave antenna.

13. The method according to claim 12, further including providing a choke configured to at least partially surround a proximate portion of the feedline.

14. The method according to claim 12, wherein the outer jacket is a metallic composite thin-walled outer jacket.

15. The method according to claim 12, wherein the outer jacket has a wall thickness less than 0.010 inches.

16. The method according to claim 12, wherein the puck forms a water-tight seal around the outer conductor.

17. The method according to claim 12, further including coupling a connection hub to the feedline, the connection hub including:

a cable connector coupled to the feedline, an inlet fluid port and an outlet fluid port defined therein; and a bypass tube configured to transition fluid proximate the cable connector to the outlet fluid port.

18. The method according to claim 12, further including:

coupling at least one inflow tube to the inlet fluid port and inserting the at least one inflow tube into the inflow hypotube for supplying the fluid thereto; and coupling at least one outflow tube to the outlet fluid port, wherein the at least one outflow tube is in fluid communication with the second hypotube for withdrawing fluid therefrom.

* * * * *